United States Patent [19]
Arnold et al.

[11] Patent Number: 5,611,810
[45] Date of Patent: Mar. 18, 1997

[54] HAIR TRANSPLANTATION APPARATUS

[75] Inventors: James E. Arnold, 24142 Big Basin Way, Saratoga, Calif. 95070; Douglas E. Dority, Sunnyvale, Calif.

[73] Assignee: James E. Arnold, Saratoga, Calif.

[21] Appl. No.: 375,312

[22] Filed: Jan. 18, 1995

Related U.S. Application Data

[63] Continuation-in-part of Ser. No. 298,823, Aug. 31, 1994, Pat. No. 5,578,054.

[51] Int. Cl.$^6$ .................................................. A61B 17/34
[52] U.S. Cl. ........................ 606/185; 606/167; 606/187
[58] Field of Search ............ 30/329–342; 606/167–185, 606/1, 108, 107

[56] References Cited

U.S. PATENT DOCUMENTS

| | | | |
|---|---|---|---|
| 803,692 | 11/1905 | Hill | 30/340 |
| 1,257,179 | 2/1918 | Berst | 30/338 |
| 2,250,237 | 7/1941 | Schwartzkopf | 30/332 |
| 2,569,286 | 9/1951 | Bunker | 30/340 |
| 4,844,070 | 7/1989 | Dee | 30/338 |
| 5,098,438 | 3/1992 | Siepser | 606/107 |

FOREIGN PATENT DOCUMENTS

| | | | |
|---|---|---|---|
| 002666978A | 3/1992 | France. | |
| 2102678 | 2/1983 | United Kingdom | 606/167 |

OTHER PUBLICATIONS

Brandy, et al., Utilization of NO–KOR Needles for Slit–Micrografting, Dermatol Surg Oncol, 1994, 20:336–339.

Charles M. Monell et al., "The Success or Failure of the Hair Transplant", Arch Otolaryngol, vol. 97, pp. 265–268, Mar. 1973.

Primary Examiner—Glenn Dawson
Attorney, Agent, or Firm—Townsend and Townsend and Crew LLP

[57] ABSTRACT

In one aspect, the invention provides a surgical handle assembly including an elongate cylindrical sheath having a proximal end, a distal end, and a central lumen therebetween. A chuck member is slidable within the sheath lumen, with the chuck member having a proximal end and a distal end. The proximal end is threaded, and a set of at least two prongs are disposed at the distal end. A threaded end element is provided for mating with the proximal threaded end of the chuck member such that rotation of the end element relative to the chuck member proximally translates the chuck member within the lumen to translate the prongs toward each other as the prongs engage the distal end of the cylindrical shaft.

7 Claims, 9 Drawing Sheets

HAIR TRANSPLANTATION APPARATUS

CROSS REFERENCE TO RELATED APPLICATIONS

This application is a continuation in part application of U.S. patent application Ser. No. 08/298,823, filed Aug. 31, 1994, now U.S. Pat. No. 5,578,054, the disclosure of which is herein incorporated by reference.

BACKGROUND OF THE INVENTION

The invention provides apparatus and methods for hair transplantation, and in particular to the formation of incisions for receiving small grafts of hair.

For many individuals, hair loss can be undesirable or even traumatic. For such individuals, many hair replacement alternatives have been proposed including wigs, hair pieces, and more recently hair transplants. To some individuals, the hair transplant alternative is particularly desirable because living hair can be used to cover bald areas. As methods for hair transplantation continue to improve, this hair replacement alternative is becoming more widely accepted.

In a typical hair transplantation procedure, grafts of skin containing hair are removed from the individual and are transplanted to other areas. To place the grafts into these areas, a number of incisions are made in the scalp. The incisions are then cleaned and a graft is inserted into each incision. When placing the grafts into the incisions, the surgeon attempts to arrange the grafts so that the resulting transplant resembles a normal hairline. To accomplish such a task, it is desirable in some cases to place only a small number of hairs, i.e. 2 to 6, often referred to as a minigraft (or even a single hair, referred to as a micrograft) into the incisions.

Over the years, a variety of techniques have been employed to transplant minigrafts. In one attempt, the use of a dilator has been proposed. According to this method, an 18 or 20 gauge hypodermic needle is employed to form an incision. A dilator is then placed in the incision to dilate the incision. After removal of the dilator, the minigraft is inserted. Over time, the incision shrinks so that the skin will support the graft. However, until the incision shrinks, the graft is unstable and can be displaced.

In other proposed methods, punches have been employed to punch a small diameter hole in the scalp. The graft is then placed in the cylindrical opening left by the punch. In yet another proposed method, a #11 blade (a Lancet blade) has been employed to form an incision for receiving a minigraft. Since the Lancet blade is angled, this method includes the additional step of translating the blade downward at an angle of 45° after the initial insertion so that the bottom of the incision has a constant depth. Having a constant depth is desirable so that the hair follicles in the graft will all be transplanted at the same depth. In a similar procedure, the use of a No-Kor vented needle (Becton Dickinson and Co, Rutherford, N.J.) has been proposed for creating incisions for receiving 1 to 3 haired minigrafts. Such a method is described in, Dominic A. Brandy and Michael Meshkin, *Utilization of No-Kor Needles For Slit-micrografting,* J Dermatol Surg Oncol, 20:336–339 (1994).

One problem associated with the above procedures is how to control the depth of the incisions. Usually, this is done visually by the surgeon when inserting the blade or punch. However, such constant visual inspection is both time consuming and tedious to the surgeon. Although the Lancet blade is angled to allow easier visual identification of the depth of the cut, use of such a blade still requires the blade to be angled downward so that the incision has a uniform depth. Such a procedure is both time consuming and inconvenient. One particular problem experienced with the use of punches is that the central lumen of the punch often becomes clogged with tissue. The punch then loses its effectiveness until the tissue is removed.

It would therefore be desirable to provide a device and method that could substantially reduce or eliminate such problems. Such a device and method should allow the depth of the incision to be easily and conveniently controlled and should not require substantial manipulation of the blade to form an incision having a constant depth. In the case of punches, the device and method should additionally allow for the creation of a plurality of incisions without having the punch becoming clogged with tissue.

SUMMARY OF THE INVENTION

The invention provides a method for transplanting hair. According to the method, an instrument is provided having a shaft and a blade that is attached to the shaft so that the blade is normal to the axis of the shaft. The blade is inserted into the skin to a preselected depth that is determined by a stop disposed along the shaft. After the incision has been formed, the instrument is removed from the skin and a graft of skin having at least one hair is placed into the incision.

The invention further provides an exemplary method for transplanting hair into a linear incision having a uniform depth. According to the method, an instrument is provided with a shaft, a linear blade that is attached to the shaft normal to the axis of the shaft, and a stop disposed along the shaft. The blade is attached to the shaft to form a sharpened distal edge on the shaft. The blade is inserted into the skin to a preselected depth that is determined by the stop. In this way, a linear incision is formed having a length defined by the length of the blade and a uniform depth along the entire length of the incision. After forming the incision, the instrument is removed from the skin and a graft of skin having at least one hair is placed into the linear incision. Preferably, the preselected depth is less than about 6 mm.

In one particular aspect of the method, the shaft is provided with two substantially parallel sides. This distance between the sides defines a thickness of the shaft. According to the method, the thickness of the shaft is varied to vary the thickness of the incision. Preferably, the thickness is varied in the range from about 0.6 mm to 0.65 mm. In another aspect, the length of the blade is varied to vary the length of the incision. Preferably, the length is varied in the range from about 1.5 mm to 2.7 mm. In yet another aspect, the preselected depth is variable and is varied by moving the stop relative to the blade.

In a further step of the method, a plurality of hairs are placed into the incision. In another aspect, a plurality of incisions are formed in the skin. By keeping the stop at a constant distance between the blade, each incision will have the same depth. Alternatively, the distance between the stop and the blade can be varied to vary the depths of the incisions.

In a preferable aspect, engagement of the stop with the skin prevents further penetration of the blade. This is accomplished by providing the instrument with an elongate handle connected to the shaft. In this way, engagement of the handle with the skin prevents further penetration of the blade.

In an alternative method for transplanting hair, an instrument having a cylindrical shaft and a concentric blade that is attached to the shaft normal to the axis of the shaft is inserted into the skin to a preselected depth as determined by a stop disposed along the shaft to form a circular incision. Preferably, the preselected depth is less than about 6 mm. The blade is attached to the shaft to form a sharpened distal edge on the shaft. Since the blade is normal to the shaft, the resulting incision is provided with a uniform depth. The instrument is then removed from the skin, and tissue from the circular incision is removed from the patient. A graft of skin having at least one hair is then placed into the incision.

In a preferable aspect, the preselected depth is variable and is varied by moving the stop relative to the blade. In yet another aspect, a plurality of hairs are placed into the incision. In another aspect, a plurality of incisions are formed in the skin. If the stop is maintained at a constant distance from the blade, each of the incisions will have substantially the same depth.

In one particular preferable aspect, engagement of the stop with the skin prevents further penetration of the blade. Engagement of the stop with the skin can be accomplished by providing the instrument with an elongate handle connected to the shaft so that engagement of the handle with the skin prevents further penetration of the blade.

In another particular aspect, a central lumen extending entirely through the shaft is provided for receiving tissue removed by the blade. Such a configuration allows for a plurality of incisions to be formed by the same instrument without having tissue accumulating near the blade to hinder the blade from forming additional incisions.

The invention provides a surgical device for forming incisions that are to receive grafts of skin having hair. The surgical device includes a elongate shaft having a proximal end and a distal end. A blade is attached to the distal end of the shaft normal to the axis of the shaft. The blade is attached to the shaft to form a sharpened distal edge on the shaft. A stop is disposed at a preselected distance from the blade for preventing penetration of the blade beyond the preselected distance. Preferably, the stop is disposed at a distance that is less than about 6 mm from the blade.

In a preferable aspect, the stop comprises a handle that is attached to the shaft. In one particular aspect, the stop is adjustable relative to the blade so that the preselected distance can be adjusted. Adjustment of the stop can be accomplished by providing an axially translatable member on the handle so that translation of the member adjusts the distance between the stop and the blade. In one exemplary aspect, the handle can be threaded so that axial translation of the member is accomplished by rotating the member around the handle.

In another preferable aspect, the blade is straight or linear and has a length in the range of about 1.5 mm to 2.7 mm. In another aspect, the shaft is rectangular in cross section and includes at least two parallel sides to define a thickness of the shaft. Preferably, the thickness in the range from about 0.6 mm to 0.65 mm.

In still another aspect, the shaft is cylindrical in geometry and has an outer diameter and an inner diameter forming a central lumen. The blade is concentric in geometry is flush with the shaft to provide a sharpened distal edge on the shaft. In this way, the central lumen can be used to receive accumulated tissue so that the surgical device can be used to form a plurality of incisions without being hindered by the accumulated tissue. Preferably, the shaft has an open proximal end which also serves as an air hole to release air when the blade is inserted into the skin.

The invention further provides a method for transplanting a single hair micrograft in a patient's scalp. According to the method, a spear-shaped blade is pressed into the scalp to form an incision having a length that is less than 2 mm and a width that is less than 0.7 mm. A single hair micrograft is then placed in the incision. In an exemplary aspect, the incision has a length of less than 1.6 mm. In a further aspect, at least a second incision is formed within about 0.5 mm to 1.0 mm from the first incision and a single hair micrograft is placed in the second incision. Use of the spear-shaped blade is advantageous in forming the second incision in such close proximity to the first incision because the spear shape of the blade provides a convenient centering point which can be visualized by the surgeon when forming the incision.

The invention provides a surgical instrument for forming a single hair micrograft incision in the skin. The instrument includes an elongate shaft having a proximal end and a distal end. A spear-shaped blade is included on the distal end of the shaft, with the blade having a length that is less than about 1.8 mm.

The invention still further provides a surgical handle assembly that includes an elongate cylindrical sheath having a proximal end, a distal end, and a central lumen therebetween. A chuck member is slidable within the sheath lumen, with the chuck member having a proximal end and a distal end. The proximal end of the chuck is threaded, and a set of at least two prongs are disposed at the distal end of the chuck. A threaded end element is provided for mating with the proximal threaded end of the chuck member and for engaging with the proximal end of the sheath. In this way, rotation of the end element relative to the chuck member proximally translates the chuck member within the lumen to translate the prongs toward each other as the prongs engage the distal end of the cylindrical sheath.

In one aspect, the central lumen has a diameter of less than 3 mm. In another aspect, an elongate shaft is provided having a proximal end and a distal end. A spear-shaped blade is on the distal end of the shaft, with the blade having a length that is less than 1.8 mm. The proximal end of the shaft is received in the prongs of the chuck member. In another aspect, an elongate cylindrical shaft is provided having a proximal end, a distal end, and an axial lumen. The shaft has a blade on its distal end, with the blade having a diameter that is less than 2 mm. The proximal end of the shaft is received in the prongs of the chuck member.

In one particular aspect, at least a portion of the sheath and the end element is knurled. In this way, the prongs can be translated toward each other by grasping the sheath with one hand and the end element with the other hand and rotating the end element.

DETAILED DESCRIPTION OF THE SPECIFIC EMBODIMENTS

Figure 1:
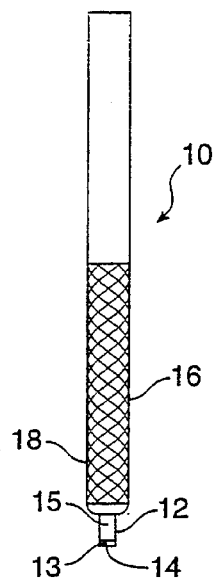
FIG. 1 illustrates a side view of a surgical device having a linear blade according to the present invention.
Figure 2:
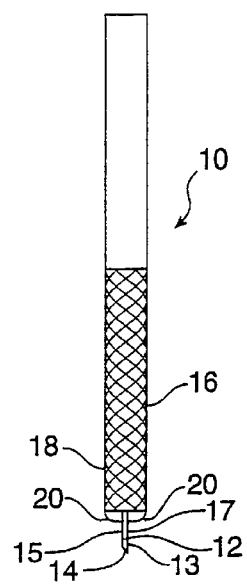
FIG. 2 illustrates the surgical device of FIG. 1 rotated at an angle of 90°.
Figure 3:
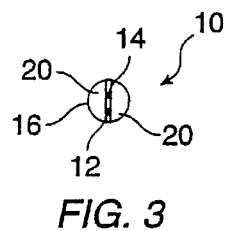
FIG. 3 is a bottom view of the surgical device of FIG. 2.

Referring to FIGS. 1–3, an exemplary embodiment of a surgical device 10 for forming linear incisions in the skin will be described. The device 10 includes a shaft 12 and a blade 14 attached to the shaft 12. The blade 14 is a "chisel" type blade and is straight, i.e. is linear, along its length. The blade 14 is "V shaped" in cross section and is attached at a distal end 13 of the shaft 12 to form a sharpened distal edge on the shaft 12. The shaft 12 is attached to an elongate handle 16 which can conveniently be provided with a gripping surface 18. Preferably, the handle 16 will have a length in the range from about 5 cm to 15 cm, more preferably at about 10 cm.

The shaft 12 and blade 14 are preferably constructed of stainless steel. The shaft 12 will preferably be rectangular in cross section (see FIG. 3) and will include at least two substantially parallel walls 15, 17. The distance between the walls 15, 17 defines a thickness of the shaft 12 which will preferably be in the range from about 0.6 mm to 0.65 mm. Such a thickness is useful in forming an incision that is wide enough to receive a graft of hair. As described in more detail hereinafter, a preferable way to vary the thickness of the shaft is simply to replace the shaft. Varying the thickness of the shaft can be desirable when using the shaft to partially dilate the incision to allow easier and faster placement of the grafts.

The length of the blade 14 will preferably be in the range from about 1.5 mm to 2.7 mm. More specifically, a length in the range from about 1.5 mm to 1.6 mm is preferable for forming incisions intended to receive a single hair micrograft. Blades having a length in the range from about 1.8 mm to 1.9 mm are preferable for forming incisions for receiving minigrafts of 2 to 3 hairs, and blade lengths in the range from about 2.5 mm to 2.7 mm are preferred for forming incisions for receiving minigrafts of 3 to 5 hairs. Blades having a length of about 1.5 mm to 1.6 mm can conveniently be formed by removing the distal end of a #61 miniblade, and blades having a length in the range from about 2.5 mm to 2.7 mm can conveniently be formed by removing the distal end of a #62 miniblade.

Figure 1A:
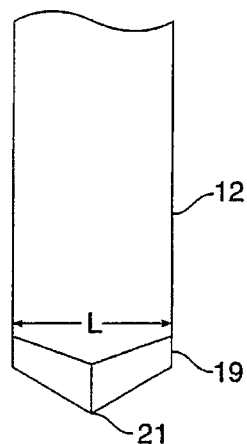
FIG. 1A illustrates a front view of an spear-shaped blade for forming micrograft incisions according to the present invention.
Figure 1B:
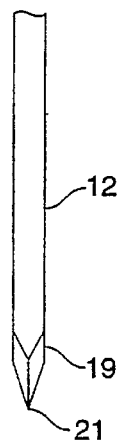
FIG. 1B illustrates a side view of the blade of FIG. 1A.

Shown in FIGS. 1A and 1B, is an alternative blade 19 for the shaft 12. The blade 19 will find its greatest use in the formation of incisions intended to receive single hair micrografts. The blade 19 has a length L that is less than about 2 mm, and will usually be substantially equivalent to that of a #61 miniblade, i.e. about 1.5 mm to 1.6 mm. Insertion of such a blade into the skin will form an incision having a length of less than about 2 mm and a width of less than about 0.7 mm. The blade 19 is spear-shaped to provide a sharp point 21 at its midpoint. The blade 19 is significantly smaller than spear point myringotomy blades, such as those commercially available from Swan Morton, which are too large to form acceptable micrograft incisions. Use of the spear-shaped blade 19 is advantageous in forming incisions for single hair micrografts because point 21 provides for ease of penetration into the skin. This allows for more rapid formation of incision and can also eliminate undesirable rotation of the blade that can sometimes occur when using a chisel type blade. The point 21 also acts as a convenient reference to allow for precise positioning of the blade prior to penetration. Such a reference is advantageous when forming incisions between two previously informed incisions that are spaced close together. For instance, the blade 19 can be used to form incisions that are within about 0.5 mm to 1.0 mm to other incisions.

Referring back to FIG. 1, the handle 16 will preferably be a conventional miniblade handle having a pair of grips 20 for receiving various sized shafts. The shaft 12 is inserted into the grips 20, and the handle is adjusted to clamp the shaft 12 within the grips 20. In this way, the distance between the blade 14 and the handle 16 can be adjusted. Preferably, the distance between the blade 14 and the handle 16 will be less than about 6 mm, and more preferably at about 5 mm. The grips 20 also allow for convenient use of various different sized blades so that a surgeon can tailor the size of the incision to the size of the intended graft.

The diameter of the handle 16 at the grips 20 is greater than the length of the blade 14. With this configuration, the handle 16 acts as a stop when the blade 14 and shaft 12 are inserted into the skin. The blade 14 and shaft 12 will penetrate into the skin until the handle 16 engages the skin. At this point, the handle 16 prevents further penetration of the blade 14 into the skin.

By configuring the surgical device 10 as previously described, a surgeon is able to preselect the depth of any incision. Once a depth is selected, a plurality of incisions that each have the same depth can rapidly and conveniently be formed in a patient without visually inspecting the depth of penetration when making each incision. By having the blade 14 being straight and normal to the axis of the shaft 12, each incision can be formed with a uniform depth along its length, i.e. the bottom of the incision is substantially parallel to the scalp at the point of incision. The blade 14 is able to create the incision having the desired depth that is uniform along its length in a single step. In contrast, Lancet blades require at least two steps to create an incision having both a desired depth and one that is uniform along its length as previously described.

Figure 3A:
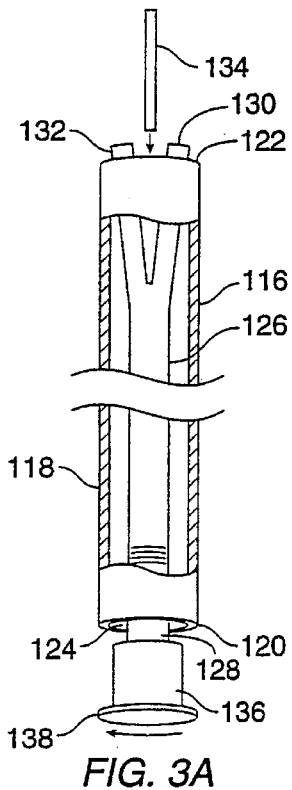
FIG. 3A illustrates an alternative handle assembly for the surgical device of FIG. 1.

An alternative handle 116 for the surgical device 10 is shown in FIG. 3A. The handle includes an elongate cylindrical sheath 118 having a proximal end 120 and a distal end 122. A central lumen 124 extends between the ends 120, 122. Slidable within the lumen 124 is a chuck member 126 having a proximal end 128 and a distal end 130. At the distal end 130 are at least two prongs 132. The prongs have a perimeter that is greater than the diameter of the lumen 124. In this way, when the chuck 126 is proximally translated within the lumen 124, the distal end 122 of the sheath 118 forces the prongs toward each other. When a shaft 134 having a blade at its distal end (not shown) is placed between the prongs 132, the shaft 134 becomes securely clamped between the prongs as the chuck 126 is drawn proximally through the lumen 124. As with the embodiment of FIG. 1, the distal end 130 of the chuck 126 functions as a stop to control the depth of blade penetration when forming an incision.

To proximally translate the chuck 126, a threaded end element 136 is provided to receive the proximal end 128 of the chuck 126 which is also threaded. The end element 136 has a proximal end 138 with a perimeter that is greater than the perimeter of the lumen 124. As the end element 136 is rotated as shown by the arrow, the proximal end 138 of the end element 136 engages the proximal end 120 of the shaft 118. At this point, further rotation of the end element 136 proximally translates the prongs 132 relative to the shaft 118. This in turn causes the prongs 132 to be translated toward each other to clamp the shaft 134. Conveniently, portions of both the shaft 118 and the end element 136 can be knurled. This allows a better gripping surface so that the shaft 118 can be grasped with one hand while the end element 136 is grasped with the other.

An advantage of the handle assembly 116 is that the prongs 132 can be made long enough to hold commercially available miniblades without alteration or modification of the miniblades. Most miniblades have relatively long shafts, and placement of a long shaft in the prongs 132 is desirable because it provides a more stable connection between the handle 116 and the miniblade. Prior art chucks include prongs that are not long enough to receive most miniblades without modifying the miniblades by removing a proximal portion of the blades, thereby reducing the stability of the blades when in the chuck.

Another advantage of the handle assembly 116 is that the end element 136 is rotated (rather than the chuck 126) to clamp the shaft 134. The end element 136 provides a convenient gripping surface so that a sufficient amount of torque can be applied. Improved torque results in greater proximal translation of the chuck, and hence a tighter grip by the prongs 132. A further advantage of the handle assembly 116 is that it can be fashioned to have a relatively small diameter. This is advantageous in allowing the surgeon to see around the handle assembly 116 when attempting to make an incision. The smaller the handle assembly, the easier a surgeon can view both the blade tip and the target location on the patient's scalp. Preferably, the central lumen will have a diameter that is less than about 3 mm. The walls of the sheath 118 will preferably be less than about 0.3 mm. Such a size provides a handle assembly 116 that is large enough to receive miniblades capable of producing incisions for receiving hair transplants having about 5 hairs or less, but small enough for a surgeon to still view the blade when performing surgery.

The prongs 132 can be fashioned so that they can receive blades having different sizes and geometries. For instance, the prongs 132 can be configured to receive cylindrical blades as described hereinafter in FIG. 4 and as described in co-pending U.S. patent application Ser. No. 08/375,313, filed on the same day as the present application, the disclosure of which is herein incorporated by reference. In this manner, the handle assembly 116 can be used for a variety of surgical applications in addition to hair transplantation, including plastic and cosmetic surgery, general surgery, and the like.

Figure 4:
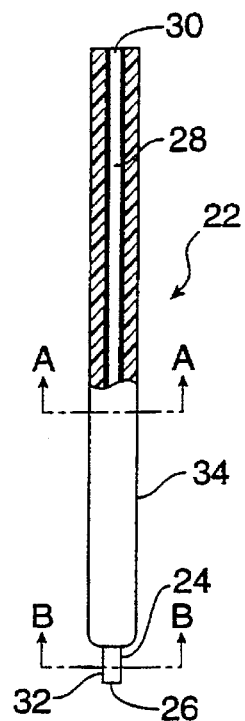
FIG. 4 is a side view of an alternative embodiment of a surgical device having a concentric blade according to the present invention.
Figure 4A:
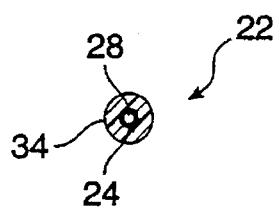
FIG. 4A is a view of the surgical device of FIG. 4 taken along lines A—A.
Figure 4B:
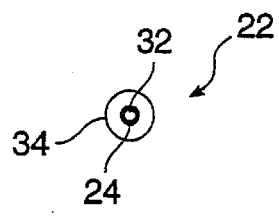
FIG. 4B is a view of the surgical device of FIG. 4 taken along lines B—B.

Referring to FIGS. 4, 4A and 4B, an alternative embodiment of a surgical device 22 will be described. The device 22 includes a cylindrical shaft 24 and a concentric blade 26 attached to the shaft 24. The shaft 24 and blade 26 form what is commonly referred to as a dermal punch. The blade 26 is attached to a distal end 32 of the shaft 24 to form a sharpened distal edge on the shaft. The cylindrical shaft 24 includes a central lumen 28 and is open both at a proximal end 30 and at the distal end 32 where the blade 26 is attached. The shaft 24 is held within a handle 34 which functions as a stop similar to the handle 16 as previously described. Preferably, the blade 26 will be distanced from the handle 34 by a distance that is less than about 6 mm, and preferably at about 5 mm. The blade 26 preferably has an outer diameter in the range from about 1.0 mm to 2.0 mm to form incisions for receiving grafts having 1 to 8 hairs.

The lumen 28 in the shaft 24 is for receiving accumulated tissue from multiple insertions of the blade 26 into the skin. When forming a plurality of incisions, tissue will often build up in the distal end 32 of the shaft 24. By extending the lumen 28 through the entire length of the shaft 24, accumulated tissue can be directed through the lumen 28 upon each additional insertion of the blade 26 to the skin. This prevents the distal end 32 from clogging and increases the effectiveness of the blade 26. The shaft 24 is open at the proximal end 30 so that an air hole can be provided in the shaft 24. This provides for easier travel of the accumulated tissue through the lumen 28. Although the shaft 24 is shown extending entirely through the handle 34, the shaft 24 can terminate anywhere within the handle 24. In such a case, the lumen 28 can be extended through the handle 34 so that an air hole will still be provided. For convenience, the handle 34 can be constructed of plastic or other disposable material so that the device can be discarded after use.

Figure 5:
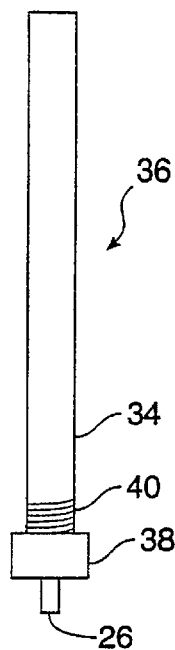
FIG. 5 is a side view of a surgical device having a variable stopping mechanism according to the present invention.

Referring to FIG. 5, an alternative embodiment of a surgical device 36 is shown. The surgical device 36 is essentially identical to the surgical device 22 of FIG. 4 except for the stopping mechanism. For convenience of discussion, the same reference numerals shown in FIG. 4 will be used to describe FIG. 5. The surgical device 36 includes an adjustable stopping mechanism that includes a rotating collar 38 that can be rotated about a plurality threads 40 provided on the handle 34. Rotation of the collar 38 translates the collar 38 axially along the handle 34 and varies the distance between the collar 38 and the blade 26. In this way, the depth of the incision can easily and conveniently be varied by simply rotating the collar 38. The collar 38 engages the skin and prevents further penetration of the blade 26. Although not shown, a variety of different mechanisms can be employed to vary the depth of the incision including adjustable clamps, slidable collars, and the like.

An adjustable collar similar to collar 38 can also be provided on the shaft 12 of the surgical device 10. Such a collar allows the depth of blade penetration to be varied as previously described.

The surgical device 36 is particularly advantageous when forming incisions over a variety of different areas on the scalp. Since the thickness of the scalp varies depending on location, the depth of blade penetration can conveniently be adjusted depending on where the incision is to be made.

Figure 6:
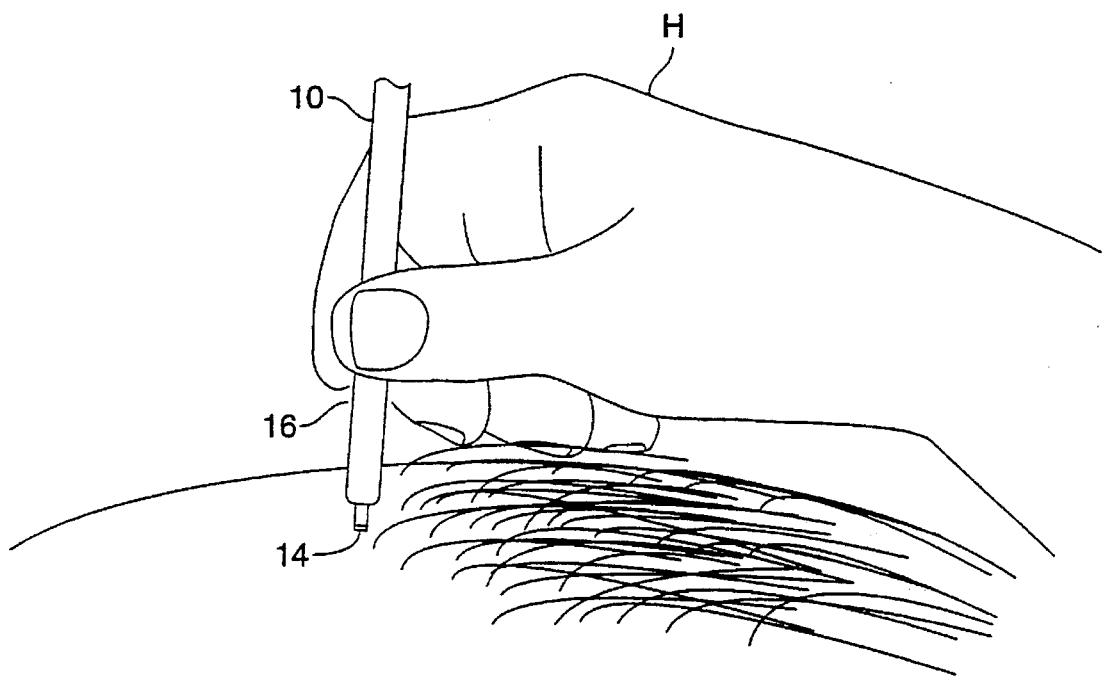
FIGS. 6–9 illustrate an exemplary method for transplanting a graft of skin having hair using a linear incision according to the present invention.
Figure 7:
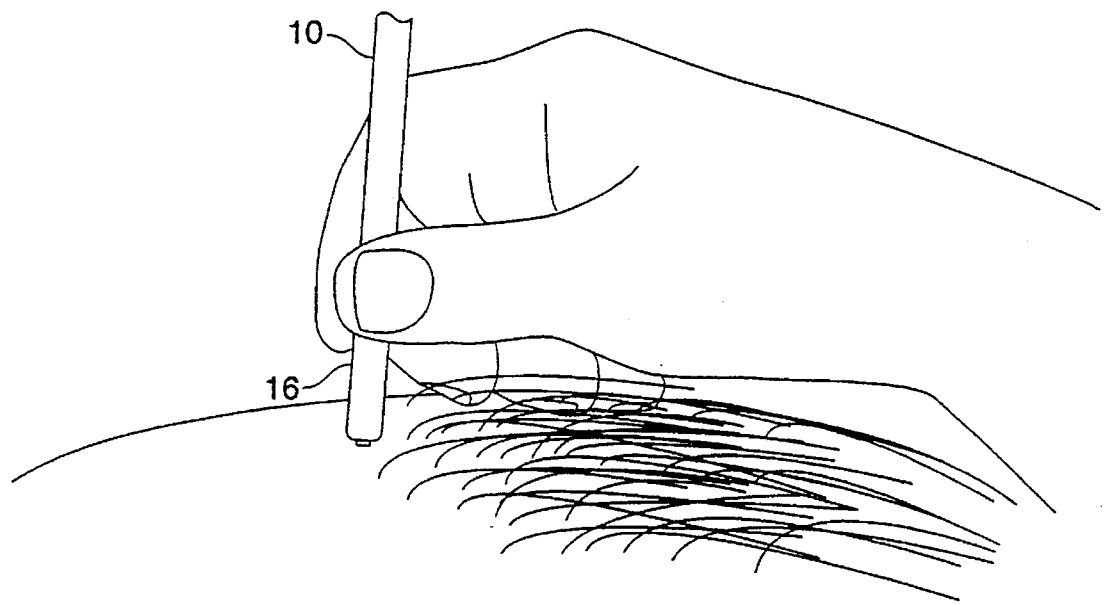
Figure 8:
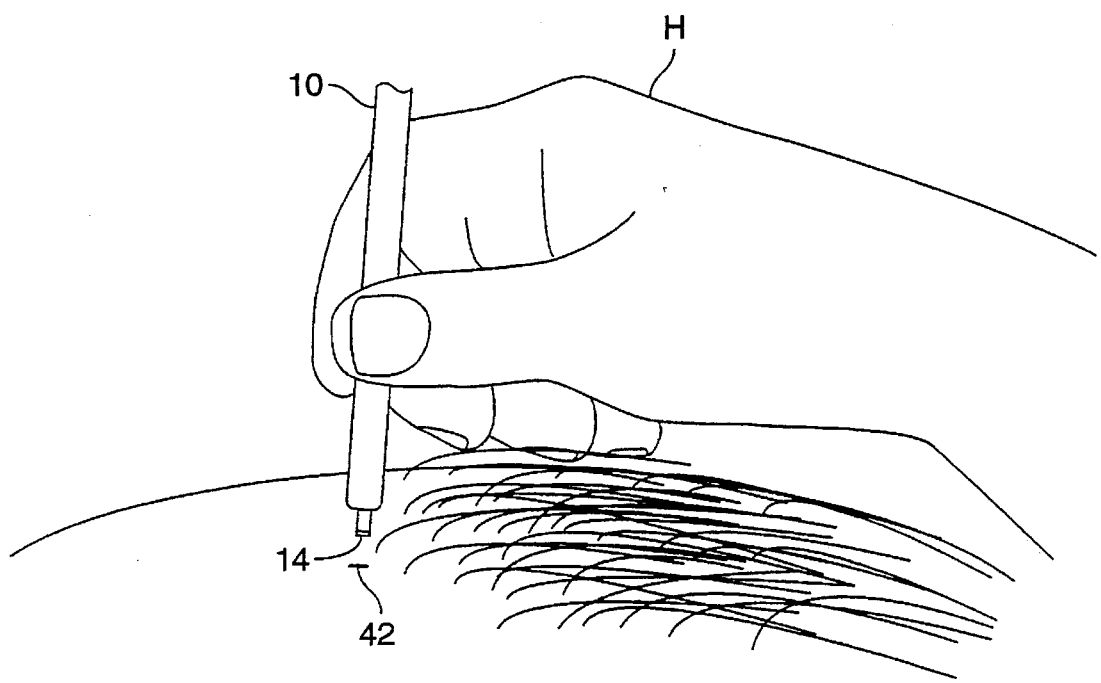
Figure 9:
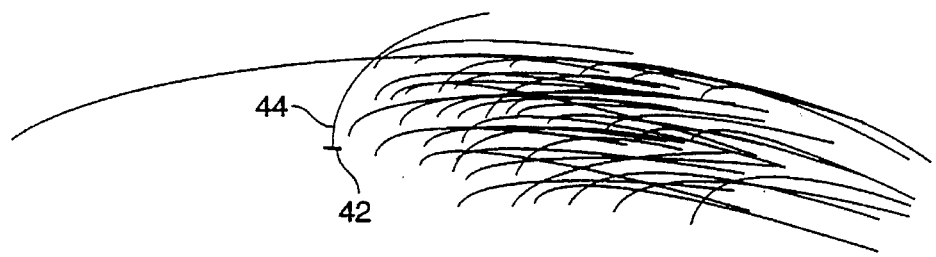

Referring now to FIGS. 6–9, an exemplary method for hair transplantation using the surgical device 10 will be described. As shown in FIG. 6, a surgeon's hand H grasps the device 10 along the handle 16 and positions the blade 14 to a desired location over the patient's scalp. As shown in FIG. 7, the blade 14 is depressed into the patient's scalp by pressing on the handle 16. When pressing the blade 14 into the skin, the handle 16 will preferably be oriented perpendicularly to the patient's scalp at the point of the incision. This allows the blade 14 (that is normal to the shaft 12 and handle 16) to produce an incision having a uniform depth along its length. Penetration of the blade 14 into the scalp is stopped when the handle 16 engages the skin. At that point, the blade 14 has reached the appropriate depth. The device 10 is then lifted from the scalp to remove the blade 14 leaving an incision 42 as shown in FIG. 8. Since the blade 14 is straight, the resulting incision 42 is linear. Having a linear incision is desirable in that it heals quickly and leaves minimal or no scarring. The incision 42 is then cleaned and a micrograft of hair 44 placed therein (see FIG. 9). Alternatively, depending on the size of the incision 42, a minigraft can be placed therein.

The process of forming the incision 42 can be rapidly repeated along the patient's hairline to form a plurality of incisions that each have substantially the same depth, and with each incision having a uniform depth along the lengths of the incisions. Each of these incisions can then have a graft of skin having hair placed therein as previously described.

Figure 10:
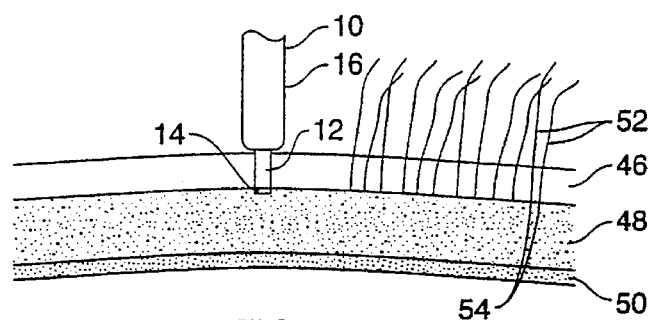
FIGS. 10–12 illustrate in greater detail the method of FIGS. 6–9 showing placement of the blade and the hair graft into the scalp.
Figure 11:
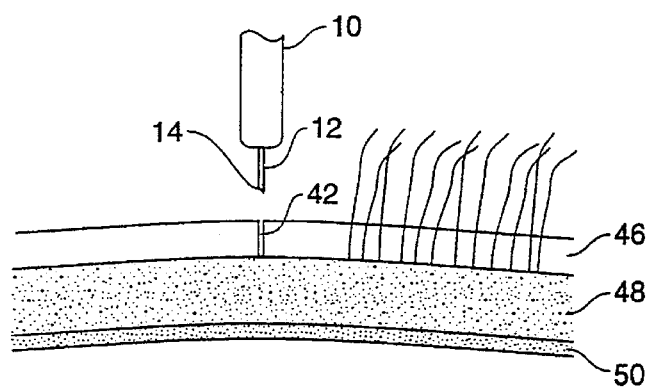
Figure 12:
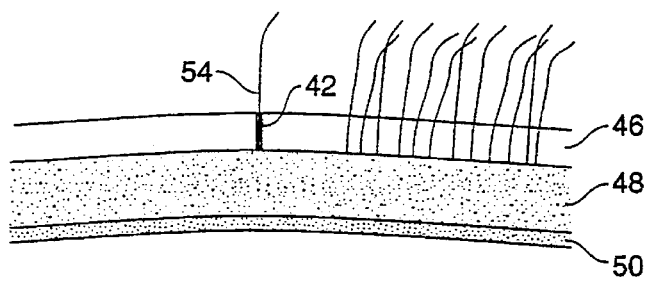

Referring to FIGS. 10–12, formation of the incision 42 will be described in greater detail. As shown in FIG. 10, the patient's scalp includes a dermis layer 46, a fat layer 48 and a galea layer 50. The patient's existing hairs 52 are disposed in the dermis layer 46 with the follicles 54 disposed at the base of the dermis layer 46, with some extending into the fat layer 48. The blade 14 is inserted through the dermis layer 46 until it reaches or slightly penetrates the fat layer 48. At this point, the handle 16 engages the dermis layer 46 and prevents further travel of the blade 14. When the device 10 is lifted from the patient's scalp as shown in FIG. 11, the formation of the incision 42 is complete. The incision has a depth that is uniform along its entire length as previously described. As shown in FIG. 12, a graft of skin having a hair 54 is placed into the incision 42 with the follicle resting near the bottom of the incision 42. As previously described, the depth of the shaft 12 can be adjusted so that the blade 14 will reach an appropriate depth which is preferably near where the dermis layer 46 and the fat layer 48 meet.

Figure 13:
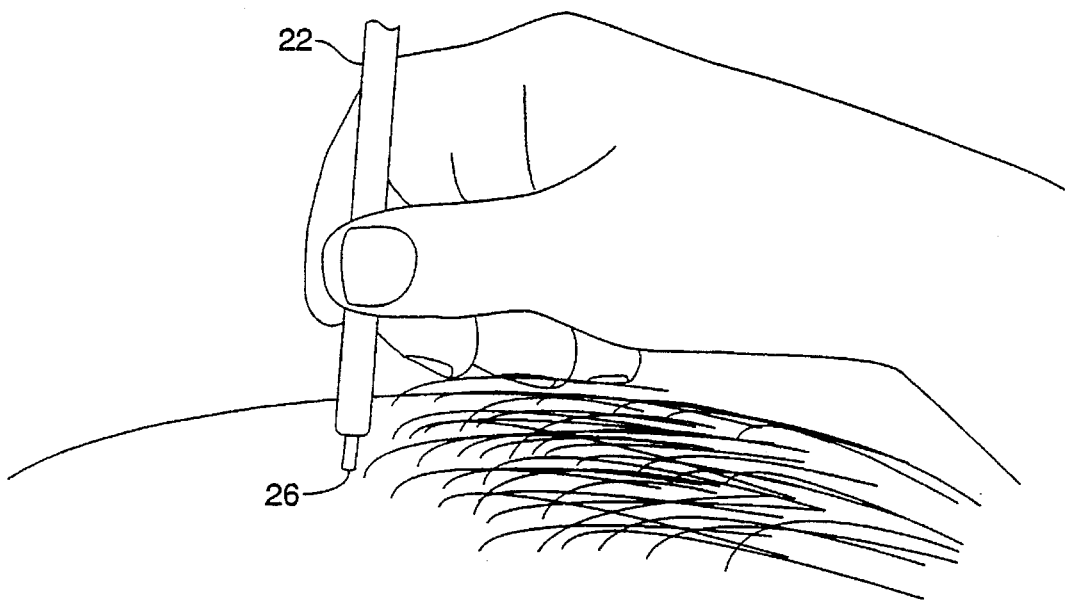
FIGS. 13–17 illustrate an alternative method for transplanting a graft of hair using a surgical device having a concentric blade.
Figure 14:
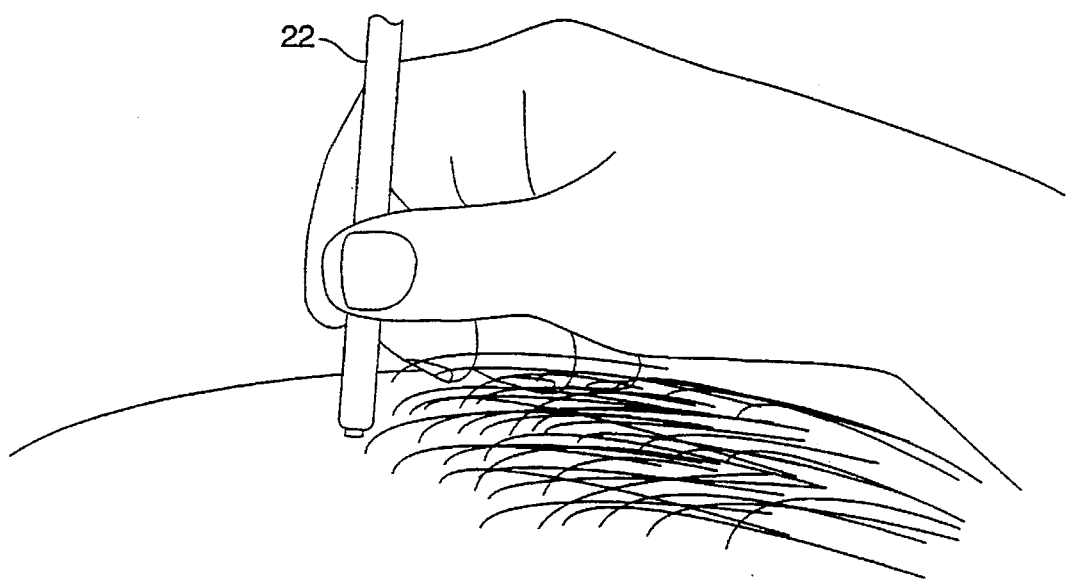
Figure 15:
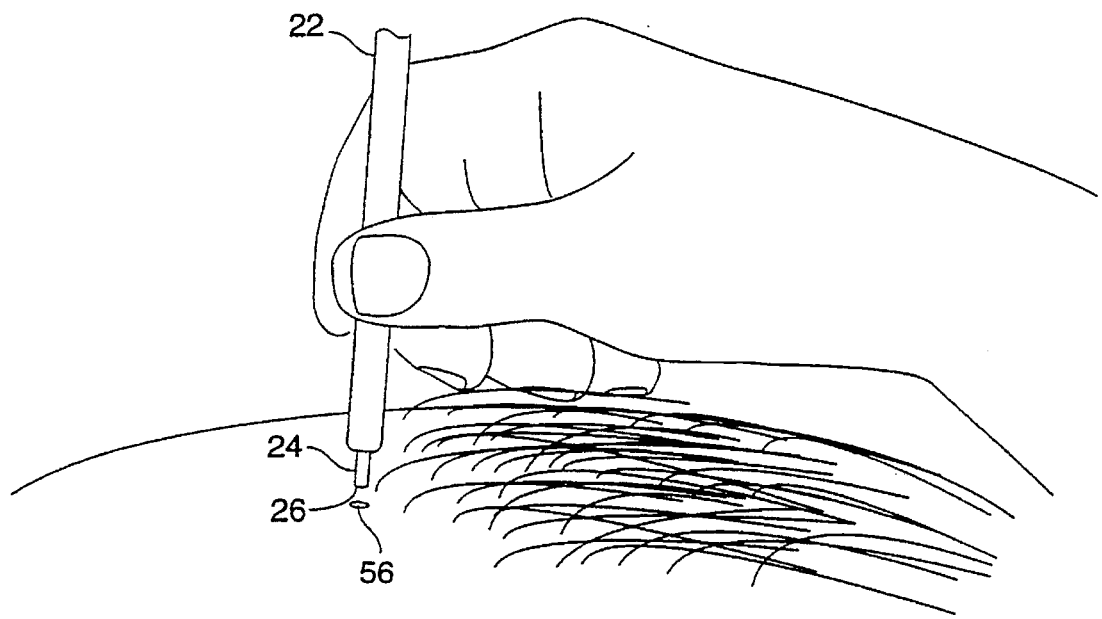
Figure 16:
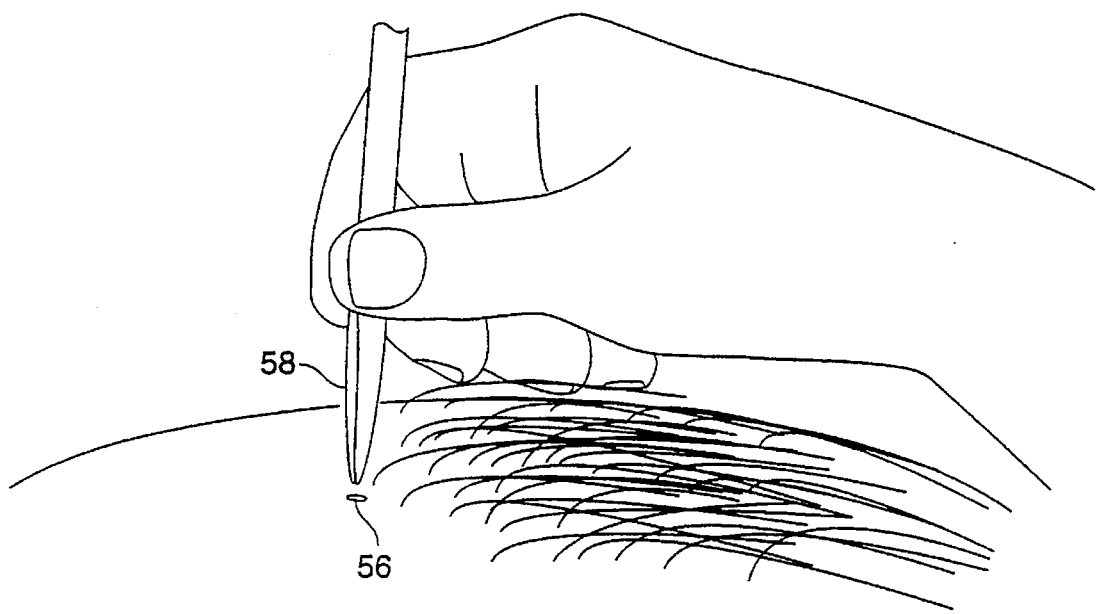
Figure 17:
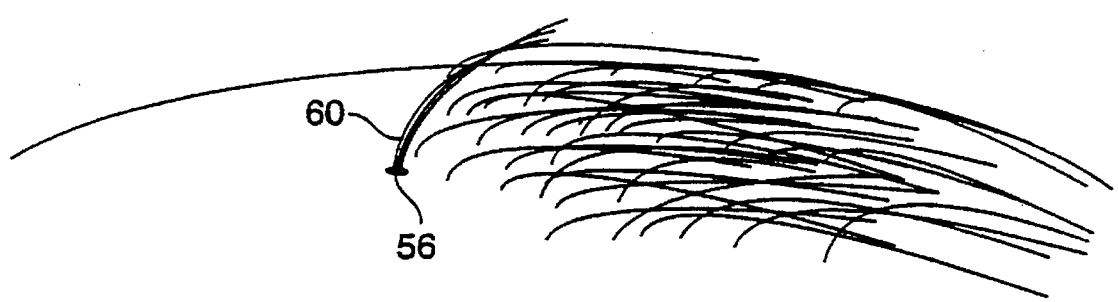

Referring to FIGS. 13–17, a method for transplanting hair using the surgical device 22 will be described. Initially, as shown in FIG. 13, the device 22 is positioned over a patient's scalp with the blade 26 near the patient's hairline. As shown in FIG. 14, the device 22 is depressed to force the blade 26 into the scalp. The device 22 is then lifted from the patient's scalp as shown in FIG. 15. In this way, a circular incision 56 is formed. Sometimes, tissue within the incision 56 will be removed by the shaft 24 when lifting the device 22 from the scalp. If not, a pair of tweezers 58 or other grasping device can be employed to remove the remaining tissue from the scalp as shown in FIG. 16. When the tissue is removed, a cylindrical hole is formed in the patient's scalp. A hair graft 60 can then be placed in incision 56 as shown in FIG. 17.

Although the foregoing invention has been described in detail by way of illustration and example, for purposes of clarity of understanding, it will be obvious that certain changes and modifications may be practiced within the scope of the appended claims.

What is claimed is:

1. A surgical cutter assembly, comprising:

an elongate cylindrical sheath having a proximal end, a distal end, and a central lumen therebetween;

a chuck member slidable within the sheath lumen, the chuck member having a proximal end and a distal end, wherein the proximal end of the chuck is threaded, and wherein a set of at least two prongs are disposed at the distal end of the chuck;

a threaded end element for mating with the proximal threaded end of the chuck member, wherein rotation of the end element relative to the chuck member while the distal end of the chuck is engaged with the distal end of the sheath proximally translates the chuck member within the lumen to translate the prongs toward each other; and an elongate shaft having a proximal end and a sharpened distal end which forms a blade for making incisions into a patient's skin, wherein the blade is spear-shaped and has a maximum length that is less than 1.8 mm, and wherein the proximal end of the shaft is received in the prongs of the chuck member.

2. The assembly of claim 1, wherein the central lumen has a diameter of less than 3 mm.

3. The assembly of claim 1, wherein at least a portion of the elongate sheath and the end element is knurled, whereby the prongs can be translated toward each other by grasping the sheath with one hand and the end element with the other hand and rotating the end element.

4. The assembly of claim 1, wherein the end element has a perimeter that is greater than a perimeter of the sheath lumen.

5. A surgical cutter assembly, comprising:

an elongate cylindrical sheath having a proximal end, a distal end, and a central lumen therebetween;

a chuck member slidable within the sheath lumen, the chuck member having a proximal end and a distal end, wherein the proximal end of the chuck is threaded, and wherein a set of at least two prongs are disposed at the distal end; and a threaded end element for mating with the proximal threaded end of the chuck member, wherein rotation of the end element relative to the chuck member while the distal end of the chuck is engaged with the distal end of the sheath proximally translates the chuck member within the lumen to translate the prongs toward each other; and an elongate shaft having a proximal end and a distal end, wherein a spear-shaped blade is on the distal end of the shaft, wherein the blade has a maximum length that is less than 1.8 mm, and wherein the proximal end of the shaft is received in the prongs of the chuck member.

6. A surgical cutter assembly, comprising:

an elongate cylindrical sheath having a proximal end, a distal end, and a central lumen therebetween;

a chuck member slidable within the sheath lumen, the chuck member having a proximal end and a distal end, wherein the proximal end of the chuck is threaded, and wherein a set of at least two prongs are disposed at the distal end of the chuck; and a threaded end element for mating with the proximal threaded end of the chuck member, wherein rotation of the end element relative to the chuck member while the distal end of the chuck is engaged with the distal end of the sheath proximally translates the chuck member within the lumen to translate the prongs toward each other; and an elongate cylindrical shaft having a proximal end, a distal end, and an axial lumen, the shaft having blade on its distal end, wherein the blade has a diameter that is less than 2 mm, and wherein the proximal end of the shaft is received in the prongs of the chuck member.

7. A surgical cutter assembly, comprising:

an elongate cylindrical sheath having a proximal end, a distal end, and a central lumen therebetween;

a chuck member slidable within the sheath lumen, the chuck member having a proximal end and a distal end, wherein the proximal end of the chuck is threaded, and wherein a set of at least two prongs are disposed at the distal end of the shaft;

a threaded end element for mating with the proximal threaded end of the chuck member, wherein rotation of the end element relative to the chuck member while the distal end of the chuck is engaged with the distal end of the sheath proximally translates the chuck member within the lumen to translate the prongs toward each other; and an elongate shaft having a proximal end and a sharpened distal end which forms a blade for making incisions into a patient's skin, wherein the shaft is cylindrical and has an axial lumen, wherein the blade has a diameter that is less than 2 mm, and wherein the proximal end of the shaft is received in the prongs of the chuck member.

* * * * *